(12) United States Patent
Tran

(10) Patent No.: US 10,918,626 B2
(45) Date of Patent: Feb. 16, 2021

(54) METHOD FOR IMPROVING PHARMACOKINETICS

(71) Applicant: Roche Palo Alto LLC, South San Francisco, CA (US)

(72) Inventor: Jonathan Q. Tran, San Francisco, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 0 days.

(21) Appl. No.: 16/842,855

(22) Filed: Apr. 8, 2020

(65) Prior Publication Data

US 2020/0230112 A1    Jul. 23, 2020

Related U.S. Application Data

(63) Continuation of application No. 16/033,177, filed on Jul. 11, 2018, now abandoned, which is a continuation of application No. 15/404,398, filed on Jan. 12, 2017, now abandoned, which is a continuation of application No. 12/766,051, filed on Apr. 23, 2010, now abandoned.

(60) Provisional application No. 61/172,722, filed on Apr. 25, 2009.

(51) Int. Cl.
    *A61K 31/426*    (2006.01)
    *A61K 31/404*    (2006.01)
    *A61K 45/06*     (2006.01)
    *A61K 31/407*    (2006.01)

(52) U.S. Cl.
    CPC .......... *A61K 31/426* (2013.01); *A61K 31/404* (2013.01); *A61K 31/407* (2013.01); *A61K 45/06* (2013.01)

(58) Field of Classification Search
    CPC .... A61K 31/426; A61K 31/407; A61K 45/06; A61K 31/404
    See application file for complete search history.

(56) References Cited

U.S. PATENT DOCUMENTS 6,037,157 A * 3/2000 Norbeck ................ A61K 38/05
                                                   435/184

FOREIGN PATENT DOCUMENTS

WO    WO2005042020    *  5/2005  ............. A61K 45/00
WO    WO2008046860    *  4/2008  ............. A61K 45/06

* cited by examiner

*Primary Examiner* — Matthew P Coughlin
*Assistant Examiner* — Thurman Wheeler
(74) *Attorney, Agent, or Firm* — Brian L. Buckwalter

(57) ABSTRACT

The object of the present invention is to inhibit oxidative metabolism of a compound of formula I by co-administration with ritonavir, a cytochrome P450 inhibitor.

6 Claims, No Drawings

METHOD FOR IMPROVING PHARMACOKINETICS

CROSS REFERENCE TO PRIOR APPLICATIONS

This application is a continuation of U.S. patent application Ser. No. 16/033,177 filed Jul. 11, 2018, which is a continuation of U.S. patent application Ser. No. 15/404,398, filed Jan. 12, 2017, which is a continuation of U.S. patent application Ser. No. 12/766,051, filed Apr. 23, 2010, which claims the benefit of priority to U.S. Provisional Application No. 61/172,722, filed Apr. 25, 2009, the contents of both are incorporated herein by reference in its entirety.

FIELD OF THE INVENTION

The present invention relates to an improved method or administering a compound according to formula I for treating HCV by co-administration with ritonavir. The invention further relates to a pharmaceutical composition containing the compound of formula I and ritonavir.

BACKGROUND

Hepatitis C virus (HCV) is the leading cause of chronic liver disease throughout the world. (Boyer, N. et al., *J. Hepatol.* 2000 32:98-112). The World Health Organization (WHO) estimates that more than 170 million people worldwide (or about 3% of the world's population) are infected with the single-stranded ribonucleic acid (RNA) HCV. (G. M. Lauer and B. D. Walker, *N. Engl. J. Med.* 2001 345:41-52) Approximately one-fifth of chronically infected patients with HCV will eventually develop cirrhosis of the liver, suffering considerable morbidity and mortality, including liver failure and hepatocellular carcinoma (T. J. Liang et al. *Ann. Intern. Med.* 2000 132:296-305; M. W. Fried et al. *N. Engl. J. Med.* 2002 347:975-982). HCV infection is the primary indication for liver transplantation in the United States (NIH Consensus Statement on Management of Hepatitis C. 2002 Jun. 10-12 19(3):146; http://www.ncbi.nlm.nih.gov/pubmed/14768714).

HCV has been classified as a member of the virus family Flaviviridae that includes the genera flaviviruses, pestiviruses, and hapaceiviruses which includes hepatitis C viruses (Rice, C. M., *Flaviviridae: The viruses and their replication.* In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of-approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forns and J. Bukh, *Clinics in Liver Disease* 1999 3:693-716; J. Bukh et al., *Semin. Liv. Dis.* 1995 15:41-63). Unfortunately type 1 infection is more resistant to therapy than either type 2 or 3 genotypes (N. N. Zein, *Clin. Microbiol. Rev.*, 2000 13:223-235).

The HCV genome encodes a polyprotein of 3010-3033 amino acids (Q. L. Choo, et al., *Proc. Natl. Acad. Sci. USA,* 1991 88:2451-2455; N. Kato et al., *Proc. Natl. Acad. Sci. USA* 1990 87:9524-9528; A. Takamizawa et al., *J. Virol.* 1991 65:1105-1113). Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. The HCV NS3 protease is a serine protease that helps process the majority of the viral enzymes, and is thus considered essential for viral replication and infectivity. These proteases are required for cleavage of specific regions of the precursor polyprotein into mature peptides. The carboxyl half of nonstructural protein 5, NS5B, contains the RNA-dependent RNA polymerase.

Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.,* 1999 19:5; Di Besceglie, A. M. and Bacon, B. R., *Scientific American,* October: 1999 80-85; G. Lake-Bakaar, *Curr. Drug Targ. Infect. Dis.* 2003 3(3):247-253; P. Hoffmann et al, *Exp. Opin. Ther. Patents* 2003 13(11):1707-1723; M. P. Walker et al., *Exp. Opin. Investing. Drugs* 2003 12(8):1269-1280; S.-L. Tan et al., *Nature Rev. Drug Discov.* 2002 1:867-881; J. Z. Wu and Z. Hong, *Curr. Drug Targ-Infect. Dis.* 2003 3(3):207-219.

Ribavirin (1-((2R,3R,4S,5R)-3,4-dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

Combination therapy of HCV with ribavirin and interferon-α ☐currently is the standard of care for treatment-naïve patients HCV. Combining ribavirin and PEG-IFN (infra) results in a sustained viral response (SVR) defined as undetectable hepatitis C virus ribonucleic acid (HCV RNA) 24 weeks after completion of therapy (M. W. Fried et al. supra) in 54-56% of patients with type 1 HCV. The SVR approaches 80% for type 2 and 3 HCV. (Walker, supra) Furthermore, PEG-IFN is given by injection, and the hematologic and constitutional toxicities of PEG-IFN and of RBV are difficult for many patients to tolerate for the long (up to 48 weeks) duration of treatment required. Currently, there is no SOC treatment for patients who either relapsed or did not respond to (nonresponders) PEG-IFN/RBV therapy. Given the high prevalence of CHC disease worldwide, the high treatment failure rate with the current SOC, and tolerability issues with the current SOC, there is a substantial unmet medical need to improve and expand therapeutic options for these patient populations. The effectiveness of the host defenses is hampered by the ability of HCV to disrupt, evade, and antagonize the host immune response, not only ensuring continued viral infection, but also quite often resisting the antiviral action of IFN therapy (M. Gale, Jr. and E. M. Foy, Nature 2005. 436:939-945). Therefore, a strategy that targets the virus itself may improve the results of therapy in comparison with current therapy options.

A number of potential new molecular targets for drug development as anti-HCV therapeutics have now been identified including, but not limited to, the NS2-NS3 autoprotease, the NS3 protease, the NS3 helicase and the NS5B polymerase. The RNA-dependent RNA polymerase is absolutely essential for replication of the single-stranded, positive sense, RNA genome. This enzyme has elicited significant interest among medicinal chemists.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCH503034 (Broceprevir, Schering), TMC435350 (Tibotec/Medivir) and ITMN-191 (Intermune). Other protease inhibitors in earlier stages of development include MK7009 (Merck), BMS-790052 (Bristol Myers Squibb), VBY-376 (Virobay), IDXSCA/IDXSCB (Idenix), BI12202 (Boehringer), VX-500 (Vertex), PHX1766 Phenomix).

SUMMARY OF THE INVENTION

In one aspect of the present invention there is provided a method for increasing the bioavailability and or blood level of a Hepatitis C virus NS3 protease inhibitor according to formula I in a patient comprising co-administering to the patient the compound of formula I and a cytochrome P450 monooxygenase inhibitor.

In another aspect of the present invention there is provided a pharmaceutical composition comprising a compound of formula I and a cytochrome P450 monooxygenase inhibitor.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "optional" or "optionally" as used herein means that a subsequently described event or circumstance may, but need not, occur, and that the description includes instances where the event or circumstance occurs and instances in which it does not.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

There is a need for compositions and therapeutic combinations for treating HCV. Combination chemotherapy has proven effective in treatment of HCV, however, patient compliance improves as the number of doses and frequency of administration decreases. Improved compounds and dosage regimens would be useful in anti-HCV therapies. The subject invention provides a method for administering a compound of formula I (R7227) and a CYP 3A4 inhibitor that enhances the bioavailability of R7227 and reduces the amount of R7227n that must be administered.

Compound I (R7227) is a highly potent and selective macrocyclic, peptidomimetic inhibitor of NS3/4A protease activity selected for development as an oral agent for the treatment of HCV infection due to the potency displayed in inhibiting NS3/4A protease. R7227 displays significant exposure in the liver of animal species, which is the primary or sole site of HCV replication in humans, and has an acceptable toxicologic profile. R7227 is a highly potent inhibitor of NS3/4A proteolysis with a 50% inhibitory concentration ($IC_{50}$)≤0.225 nM and a high degree of specificity for the intended target. In cell-based potency assays employing a genotype 1 HCV replicon, R7227 has an $IC_{50}$ of 1.77 nM. R7227 additionally displays synergistic antiviral effects with polyethylene glycol conjugated ("pegylated") interferon alfa-2a (PEG-IFN-α2a, Pegasys®, Roche) in this same cell-based assay that suggests R7227 will be useful in HCV therapy.

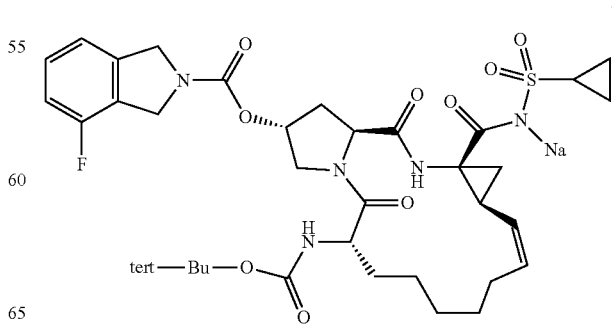

Cytochromes, especially the CYP3A4 isoform, have been found to metabolize R7227 resulting in a requirement for more frequent and higher dose levels to maintain therapeutically effective blood levels.

In early preclinical studies, cytochrome P450 phenotyping using chemical inhibitors suggests that multiple CYP isozymes including 3A4, 2C19, 1A2, 2D6, and 2C9 participate in the metabolism of (R7227). Further experiments with recombinant CYPs show that only CYP3A4 metabolized R7227 to an extent that could influence the pharmacokinetics. Therefore, a cytochrome P450 monooxygenase inhibitor in an amount effective to inhibit metabolism of the protease inhibitor could increase the bioavailability of R7227 compared to administration in the absence of the CYP inhibitor.

Some drugs are metabolized by cytochrome P450 enzymes. These enzymes typically oxidize the drugs resulting in unfavorable pharmacokinetic characteristics (e.g., decreased blood levels, decreased half-life). In these cases inhibition of drug metabolism can lead to improvements in the pharmacokinetic profile of the drug. (see, e.g., U.S. Pat. No. 6,037,157; D. E. Kempf et al. *Antimicrob. Agents Chemother.*, 1997 41:654-660; W. J. Curatolo and G. Foulds, U.S. Patent Publication 2004/0091527 and M. G. Cordingley, U.S. Patent Publication US2004/0152625). To ascertain whether combination therapy with a cytochrome P450 antagonist will improve the pharmacokinetics of a drug the metabolic pathways involved must be elucidated.

Cytochrome P450 (CYP P450) is a very large and diverse superfamily of hemoproteins. Both exogenous and endogenous compounds as substrates for cytochrome P450 isoforms. Cytochrome P450 3A4 (CYP3A4; EC 1.14.13.97), is one of the most important enzymes involved in the metabolism of xenobiotics in the body. CYP3A4 is involved in the oxidation of the largest range of substrates of all the CYPs. Although CYP3A4 is predominantly found in the liver, it is also present in other organs and tissues of the body.

Any CYP inhibitor that improves the pharmacokinetics of the relevant NS3 protease may be used in a method of this invention. These CYP inhibitors include, but are not limited to, ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine and erythromycin. A preferred CYP inhibitor is ritonavir.

Ritonavir is a potent inhibitor of CYP3A4 activity and is currently utilized at low non-therapeutic doses (e.g., 100 mg twice daily) to enhance or "boost" the PK of other HIV protease inhibitors (PIs). Given the high prevalence of HIV/HCV co-infection, R7227 could be used for the treatment of HCV in HIV/HCV co-infected patients who received ritonavir-boosted HIV PIs, resulting in possible interactions between ritonavir-boosted HIV PIs and R7227.

However, in addition to the inhibitory effect on 3A4, ritonavir appears to induce the activities of other enzymes including CYPs 1A2, 2C9, and 2C19. Although during acute dosing, the inhibitory effect of ritonavir will be predominant resulting in elevated levels of R7227, chronic dosing anticipated in HCV therapy could induce other isoforms which could oxidize R7227 offsetting the desired inhibitory effect.

In one embodiment of the present invention there is provided a method for increasing the bioavailability of Hepatitis C virus NS3/4A protease inhibitor R7227 in a patient in need thereof comprising administering R7227 and a cytochrome P450 monooxygenase inhibitor wherein the amount of the cytochrome P450 monooxygenase inhibitor is sufficient to elevate the blood levels of R7227 compared to the blood levels R7227 in the absence of a cytochrome P450 monooxygenase inhibitor.

In another embodiment of the present invention there is provided a method for increasing the bioavailability of R7227 in a patient comprising administering R7227 and ritonavir. Ritonavir is marketed by Abbott Laboratories under the name of NORVIR® as an HIV protease inhibitor (Chemical Abstract Registry Number 1555213-67-5).

In another embodiment of the present invention there is provided a method for increasing the bioavailability of R7227 in a patient comprising co-administering R7227 and ritonavir wherein R7227 and ritonavir are in a separate dosage form. The doses of each can be taken either at or about the same time or the doses may be taken at different intervals.

In another embodiment of the present invention there is provided a method for increasing the bioavailability of R7227 in a patient comprising co-administering R7227 and ritonavir wherein R7227 and ritonavir are administered simultaneously. R7227 and ritonavir may be present in a single formulation for increased patient convenience.

In another embodiment of the present invention there is provided a method for increasing the bioavailability of R7227 in a patient comprising co-administering R7227 and ritonavir wherein R7227 and ritonavir are administered in a single dosage form.

In another embodiment of the present invention there is provided a method for increasing the bioavailability of R7227 in a patient comprising co-administering a dose of 25 to 600 mg/day of R7227 and 50 to 400 mg/day of ritonavir.

In another embodiment of the present invention there is provided a method for increasing the bioavailability of R7227 in a patient comprising co-administering a dose of 50 to 300 mg/day of R7227 and 100 to 200 mg/day of ritonavir.

In a another embodiment of the present invention there is provided a method for treating HCV comprising administering to a patient in need thereof the compound of formula I, or free base or other pharmaceutically acceptable salt thereof, and a cytochrome P450 monooxygenase inhibitor.

In a another embodiment of the present invention there is provided a method for treating HCV comprising administering to a patient in need thereof the compound of formula I, or free base or other pharmaceutically acceptable salt thereof, and ritonavir.

Combination therapy has proven to be a valuable component of antiviral therapy and therefore treatment of HCV with R7227 and ritonavir may comprise administration of another component comprising an additional agent selected from an immunomodulatory agent; an antiviral agent; another HCV protease inhibitor; an inhibitor of another target in the HCV life cycle; such as an HCV polymerase inhibitor or combinations thereof.

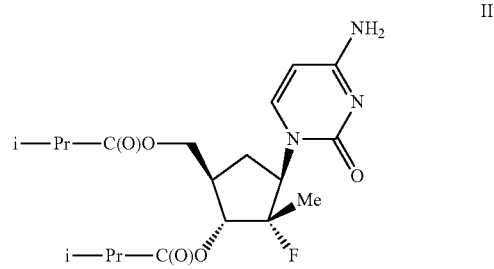

In another embodiment of the present invention there is provided a method for treating HCV comprising co-administering along with a compound of formula I and ritonavir at least one additional agent selected from an immunomodulatory agent and/or an antiviral agent and/or another inhibitor of HCV NS3/4A protease and/or an inhibitor of NS5B polymerase and/or a broad-spectrum viral inhibitor and/or another cytochrome P-450 inhibitor.

In another embodiment of the present invention there is provided a method for treating HCV which method comprises co-administering II (R7128) along with R7227 and ritonavir.

In still another embodiment of the present invention there is provided a method for treating HCV which method comprises co-administering α-, β- or γ-interferon and/or thymosin and/or ribavirin and/or R7128 along with R7227 and ritonavir.

In a another embodiment of the present invention there is provided a pharmaceutical composition comprising R7227 or a pharmaceutically acceptable salt thereof, a cytochrome P450 monooxygenase inhibitor or a pharmaceutically acceptable salt thereof, and at least one pharmaceutically acceptable excipient, diluent or carrier.

In a another embodiment of the present invention there is provided a pharmaceutical composition comprising R7227, or free base or other pharmaceutically acceptable salt thereof, a cytochrome P450 monooxygenase inhibitor, and at least one pharmaceutically acceptable excipient, diluent or carrier.

In yet another embodiment of the present invention there is provided a comprising R7227, or free base or other pharmaceutically acceptable salt thereof, a cytochrome P450 monooxygenase inhibitor, the HCV polymerase inhibitor R7128 and at least one pharmaceutically acceptable excipient, diluent or carrier.

In a another embodiment of the present invention there is provided a pharmaceutical composition comprising R7227, or free base or other pharmaceutically acceptable salt thereof, ritonavir, or a pharmaceutically acceptable salt thereof, and at least one pharmaceutically acceptable excipient, diluent or carrier.

In a fifteenth embodiment of the present invention there is provided a kit comprising a Hepatitis C virus NS3 protease inhibitor according to formula I and ritonavir.

In an embodiment of the present invention there is provided a pharmaceutical pack containing comprising a compound according to formula I, ritonavir, and optionally an informational insert containing directions for the use of the inhibitors.

Ritonavir low dose was reported to increase the exposure of midazolam, the most sensitive CYP3A probe substrate, by approximately 7-fold. (A. A. Mathias et al., *Clin. Pharmacol. Ther.* 2009 85(1)64-70). SimCYP® simulation (SymCYP Limited, Blades Enterprise Centre, John Street, Sheffield S2 4SU, UK) predicted that ritonavir could increase R7227 exposure between ca. 2- and 4-fold, assuming the contribution of CYP3A to the overall elimination of R7227 is 50% and 100%, respectively. When co-administered with ritonavir in this study, the predicted 4-fold increase in R7227 exposure is still significantly lower than that observed at the highest safe and tolerable dose of 1600 mg in the SAD study in healthy volunteers.

Multiple doses of ritonavir 100 mg every 12 hours significantly increased R7227 $AUC_{0\to\infty}$, $C_{max}$, and $C_{12h}$ by approximately 5.5-fold, 3.25-fold, and 27- to 42-fold, respectively. The multiple-dose effect of ritonavir on R7227 $C_{12}h$ is less than that of the acute single-dose effect of ritonavir possibly due to the induction of CYP enzymes by ritonavir following multiple dosing offsetting some of the acute inhibitory effect by ritonavir on CYP 3A4. Thus the pharmacokinetics R7227 was substantially improved by the co-administration of ritonavir.

Dosage and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The methods described herein comprise administration of combinations of a Hepatitis C virus NS3/4A protease inhibitor and a cytochrome P450 monooxygenase inhibitor. Such administration is referred to herein as co-administration. Co-administration includes administering each inhibitor in the same dosage form or in different dosage forms. When administered in different dosage forms, the inhibitors may be administered at the same or at different times and in any order. Accordingly, this invention provides methods wherein the CYP inhibitor is administered together with the Hepatitis C virus NS3/4A protease inhibitor in the same dosage form or in separate dosage forms.

If the CYP inhibitor and protease inhibitor are administered in separate dosage forms, each inhibitor may be administered about simultaneously. Alternatively, the CYP inhibitor may be administered in any time period around administration of the protease inhibitor. That is, the CYP inhibitor may be administered prior to, together with, or following the NS3/4A protease inhibitor. The time period of administration should be such that the CYP inhibitor affects the metabolism of the protease inhibitor. For example, if the protease inhibitor is administered first, the CYP inhibitor should be administered before the protease inhibitor is metabolized and/or excreted The term "therapeutically effective amount" as used herein means an amount required to reduce symptoms of the disease in an individual. The level therapeutic of effectiveness in HCV therapy is generally determined by measuring the levels of viral RNA. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved.

Dosage levels of between about 100 and about 800 mg per day, preferably between about 200 and about 600 mg per day of the NS3 protease inhibitor are useful for the prevention and treatment of HCV mediated disease. For the CYP inhibitor, the dosage levels of between about 50 to about 400 mg per day, would be typical. More typical would be dosage levels of between about 100 to about 200 mg per day. Typically, the pharmaceutical compositions of, and according to, this invention will be administered from about 1 to about 2 times per day. The amount of active ingredient that may be combined with the carrier materials to produce a single dosage form will vary depending upon the host treated and the particular mode of administration. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

For preferred dosage forms of ritonavir have been disclosed by L. A. Al-Razzak et al. in U.S. Pat. No. 5,484,801 published Jan. 16, 1996, U.S. Pat. No. 5,948,436 published Sep. 7, 1999, WO 95/07696 published Mar. 23, 1995 and WO 95/09614 published Apr. 13, 1995.

The methods described herein comprise administration of combinations of a Hepatitis C virus NS3 protease inhibitor and a cytochrome P450 monooxygenase inhibitor. Such administration is referred to herein as co-administration. Co-administration includes administering each inhibitor in the same dosage form or in different dosage forms. When administered in different dosage forms, the inhibitors may be administered at the same or at different times and in any order. Accordingly, this invention provides methods wherein the CYP inhibitor is administered together with the Hepatitis C virus NS3/4A protease inhibitor in the same dosage form or in separate dosage forms.

If the CYP inhibitor and protease inhibitor are administered in separate dosage forms, each inhibitor may be administered about simultaneously. Alternatively, the CYP inhibitor may be administered in any time period around administration of the protease inhibitor. That is, the CYP inhibitor may be administered prior to, together with, or following the NS3/4A protease inhibitor. The time period of administration should be such that the CYP inhibitor affects the metabolism of the protease inhibitor. For example, if the protease inhibitor is administered first, the CYP inhibitor should be administered before the protease inhibitor is metabolized and/or excreted Combination therapy has proven to be a valuable component of antiviral therapy and therefore treatment of HCV with R7227 and ritonavir may comprise administration of another component comprising an additional agent selected from an immunomodulatory agent; an antiviral agent; another HCV protease inhibitor; an inhibitor of HCV polymerase or another target in the HCV life cycle or combinations thereof.

Pharmaceutical compositions may also be prescribed to the patient in "patient packs" containing the whole course of treatment in a single package, usually a blister pack. Patient packs have an advantage over traditional prescriptions, where a pharmacists divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions.

Administration of the combination of the invention by means of a single patient pack, or patient packs of each formulation, containing within a package insert instructing the patient to the correct use of the invention is a desirable additional feature of this invention which can improve patient compliance.

According to a further aspect of the invention is a pack comprising at least a NS3 protease inhibitor and a CYP 3A4 inhibitor of the invention and an information insert containing directions on the use of the combination of the invention. In an alternative embodiment of this invention, the pharmaceutical pack further comprises one or more of additional agent as described herein. The additional agent or agents may be provided in the same pack or in separate packs.

Another aspect of this involves a packaged kit for a patient to use in the treatment of HCV infection or in the prevention of HCV infection, comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a NS3/4A protease inhibitor and a CYP inhibitor (and optionally an additional agent) or derivatives thereof are prepared in a conventional manner. Typically, such a kit will comprise, e.g. a composition of each inhibitor and optionally the additional agent(s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

In order that this invention be more fully understood, the following preparative and testing examples are set forth. These examples are for the purpose of illustration only and are not to be construed as limiting the scope of the invention in any way.

Example

Pharmacokinetic Enhancement of R7227 in Healthy Adults

Subjects were screened for participation in this study within 21 days before dosing. The study enrolled 14 healthy volunteers (n=14 per group). The dosing schedule is illustrated below:

TABLE I

| Procedure | Study Day | | | | |
|---|---|---|---|---|---|
| | 1 | 2 | 3 | 4 to 11 | 12 |
| R7227 dosing[1] | x | | x | | x |
| Ritonavir Dosing[2] | | | x | x | x |
| PK collections | 24-h PK | | 48-h PK | | 48-h PK |

[1]R7227 100 mg single oral dose
[2]Ritonavir 100 mg dose orally every 12 h.

R7227 Formulation—

R7227 was formulated into clear size 10 oval soft gelatin capsules for oral administration at a strength of 100 mg per capsule (anhydrous free acid equivalent). The capsule fill solution consists of R7227-001, polyethylene glycol PEG400 (Macrogol 400), and butylated hydroxytoluene (BHT). All excipients are compendial grade (NF or EP). Gelatin Type 195 (NF, EP) is used as the bulk gel mass for the capsule shell, with small amounts of sorbitol liquid 85/70/00 (NF, EP) and water (USP) used as plasticizers.

All study medications were with a meal. On the R7227 administration days (alone or with ritonavir), study medications were administered after completion of a standard high-fat breakfast and the breakfasts on these days were identical. R7227 was administered orally as a single dose of a 100 mg soft gel capsule on days 1, 3 and 12. On days 3 and 12, R7227 was administered with the morning dose of ritonavir. Ritonavir 100 mg was administered orally twice daily (every 12 hours) from day 3 to day 12.

Blood samples (5 mL) were collected to determine plasma concentrations of R7227 (and metabolites when assays were available) according to the following schedule Day 1, PK samples (5 mL) were be collected before R7227 dosing (predose) and at 0.5, 1, 1.5, 2, 2.5, 3, 3.5, 4, 6, 8, 12, and 24 hours after R7227 dosing;

Days 3 and 12, PK samples (5 mL) were collected before R7227 dosing (predose) and at 0.5, 1, 1.5, 2, 2.5, 3, 3.5, 4, 6, 8, 12, 24, 36, and 48 hours after R7227 dosing.

Primary PK parameters of R7227 that were determined are $C_{max}$ and $AUC_{0 \to \infty}$. Secondary PK parameters of R7227 that were measured include $T_{max}$ and $AUC_{0 \to last}$, CL/F, $t_{1/2}$, $C_{12\,hr}$ and $C_{24\,h}$.

Analysis of variance (ANOVA) was applied to the log-transformed primary pharmacokinetic parameters. Two-sided 90% confidence intervals for the ratios of the geometric means of the primary parameters ($AUC_{0 \to \infty}$ and $C_{max}$ of R7227) were derived for the following comparisons: (R7227+Ritonavir) Day 3 versus R7227 Day 1 and (R7227+Ritonavir) Day 12 versus R7227 Day 1

Analysis of variance (ANOVA) was used to analyze all primary study parameters using the following model:

$$Yij = \mu + \tau i + sj + \varepsilon ij$$

where Yij denotes the PK parameter to be analyzed, $\mu$ denotes the general mean of the transformed variable, $\tau i$, the fixed effect of treatment; sj the random effect of subject; $\varepsilon ij$ (error). The random deviations $\varepsilon ij$ are assumed to be independent and normally distributed with zero mean and common variance $\sigma^2$. The group comparisons $\tau$ R7227+Ritonavir$-\tau$R7227, the residual variance $\sigma^2$, and the 90% confidence limits for the group comparisons were estimated from the ANOVA model. For log-transformed variables ($AUC_{0 \to \infty}$ and $C_{max}$), the ratio of true group means and the confidence limits for the corresponding ratio of means of the untransformed variables will be calculated by exponentiation of the least squares means differences and the confidence limits for the transformed values, respectively.

TABLE II

| R7227 PK (unit) | N | Day 1 (Alone) | Geometric Least Square Mean (GLSM) Day 3 (with Ritonavir single dose) | Day 12 (with Ritonavir multiple dose) | Ratio of GLSM (90% CI) Day 3 vs Day 1 | Day 12 vs Day 1 |
|---|---|---|---|---|---|---|
| $AUC_{0 \to \infty}$ ng*h/mL | 12 | 14.4 | 82. | 79.4 | 5.70 (4.07, 7.99) | 5.50 (4.05, 7.48) |
| $C_{max}$ (ng/mL) | 12 | 8.40 | 26.4 | 27.3 | 3.14 (1.87, 5.25) | 3.25 (2.12, 4.96) |
| $C_{12\,h}$ (ng/mL) | 8[a] | 0.02 | 1.00 | 0.53 | 50.6 (25.6, 100) | 26.9 (17.7, 41.0) |
| $C_{12\,h}$ (ng/mL) | 12[b] | 0.01 | 0.55 | 0.36 | 65.2 (34.8, 122) | 42.4 (25.7, 70.0) |

[a]Non-missing, non-BLQ (0.010 ng/mL) data from all three treatment days. (BLQ = Below Limit of Quantitation)
[b]Include extrapolated $C_{12\,h}$ values from 4 subjects with BLQ values on day 1

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

I claim:
1. A method of treating a Hepatitis C virus infection in a patient in need thereof comprising

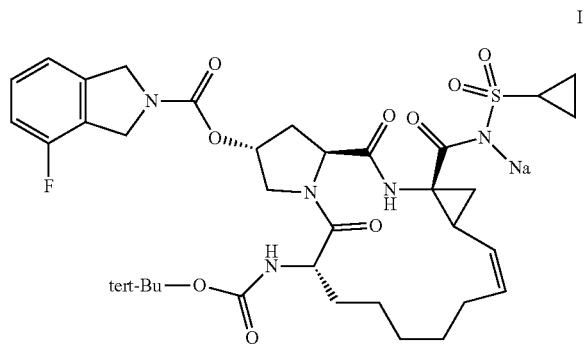

I administering the compound of formula I as a free base or a pharmaceutically acceptable salt thereof and ritonavir wherein the dose of ritonavir is 50 to 400 ma/day and the dose of compound I was 25 to 600 ma/day.

2. The method according to claim 1 wherein the separate dosage forms are administered about simultaneously.

3. The method according to claim 1 wherein the compound of formula I and ritonavir are administered in a single dosage form.

4. A method according to claim 1 wherein the dose of ritonavir is 100 to 200 mg/day and the-dose of compound I was 50 to 300 mg/day.

5. The method according to claim 1 which method comprises co-administering the compound of formula I and ritonavir and at least one additional agent selected from an immunomodulatory agent and/or an antiviral agent and/or another inhibitor of HCV NS3/4A protease and/or an inhibitor of NS5B polymerase and/or a broad-spectrum viral inhibitor and/or another cytochrome P-450 inhibitor.

6. The method according to claim 5, wherein said immunomodulatory agent is α-, β- or γ-interferon or thymosin, said antiviral agent is ribavirin or said polymerase inhibitor is R7128.

* * * * *